United States Patent [19]
de Monts

[11] Patent Number: 5,159,699
[45] Date of Patent: Oct. 27, 1992

[54] 3D INTEGRATED GUIDING STRUCTURE

[75] Inventor: Humbert de Monts, Paris, France

[73] Assignee: Thomson-CSF, Puteaux, France

[21] Appl. No.: 668,783

[22] Filed: Mar. 13, 1991

[30] Foreign Application Priority Data

Mar. 27, 1990 [FR] France .................. 90 03878

[51] Int. Cl.[5] ........................................... G02B 6/10
[52] U.S. Cl. ....................................... 385/14; 385/15;
385/130; 385/131; 385/42; 385/50
[58] Field of Search ............... 385/129, 130, 132, 14,
385/15, 42, 43, 50

[56] References Cited

U.S. PATENT DOCUMENTS 4,901,321  2/1990  Blondeau et al. .................. 385/130
4,952,015  8/1990  Van Ruyven ....................... 385/130

FOREIGN PATENT DOCUMENTS 3815293  11/1989  Fed. Rep. of Germany .
2174212  10/1986  United Kingdom .

OTHER PUBLICATIONS

Journal of Applied Physics, 66, No. 5, Sep. 1, 1989, pp. 2200-2205, L. C. So, et al., "A New Integrable Optical Modulator-Switch Optimized for Speed and Power Consumption".

Primary Examiner—Georgia Y. Epps
Attorney, Agent, or Firm—Oblon, Spivak, McClelland, Maier & Neustadt

[57] ABSTRACT

In an optic coupler, two guides made in the thickness of a substrate are located in two distinct planes. They have sinuous configuration so as to have at least one coupling zone perpendicularly to the planes of the guides. Application: optic switching.

12 Claims, 4 Drawing Sheets

3D INTEGRATED GUIDING STRUCTURE

BACKGROUND OF THE INVENTION

1. Field of the Invention

The invention concerns a 3D integrated guiding structure and, more particularly, a structure made of a semiconductor material as well as the method of its manufacture.

2. Description of the Prior Art

The making of guides with inter-guide coupling calls for a degree of precision that is difficult to obtain in known techniques owing to the limitations of microlithography techniques.

The invention enables the making of optic guides in which it is possible to achieve precise adjustment of the distance of the guides in the coupling zones.

Furthermore, at the present time, semiconductors have great potential as basic materials for the making of optoelectronic components. The growth techniques (MOCVD or MBE) used enable the thicknesses to be controlled to within a few angstroms, and enable the growth of different types of semiconductors on the same substrate. The interfaces between two different semiconductor layers may be abrupt and of very high crystallographic quality, inducing very low optic losses. At present, the propagation losses are smaller than 0.2 dB/cm (Cf. Y. Bourbin et al, *Very Low Loss Waveguides And Efficient Modulators In InGaAsP/InP*, Proceedings of the IGWO Conference in Boston, U.S.A., February 1989, pp. 110-112).

Furthermore, at the present time, the techniques of microlithography and the processes of selective chemical attack enable the making of micron-sized patterns. Selective chemical attack is controlled by means of a barrier layer, and it is common to make strips with a thickness of some tens of angstroms and a width of about one micron on a length of several centimeters.

Thus, the association of these two techniques currently enables the making of the structure described in the present invention.

The state of the art of optoelectronic components enables the setting up of functions that can be fulfilled by the structure described in the invention. However, the promising nature of the invention lies in the compactness, the performance characteristics and the multifunctional character of the structure and its very simple method of manufacture.

The invention provides a solution to the problem of 3D integration for it makes use of the vertical dimension. The idea is to use the coupling of light vertically in a bimodal structure and to use the processes of lithography for the two plane dimensions.

The multifunctional character arises from the properties of the directional couplers with the particular feature, in the case of this structure, of having very short coupling lengths. This is a major advantage for wavelength multiplexing or demultiplexing. By contrast, for the light modulation, the effects may be boosted by the presence, in the structure, of highly active materials such as multiple quantum wells (MQW).

The structure of the invention therefore has the following advantages:
- 3D integration;
- Multifunctional character;
- Performance characteristics;
- Easy manufacture;
- Simplicity.

SUMMARY OF THE INVENTION

The invention therefore concerns a 3D integrated guiding structure comprising at least two waveguides positioned respectively in a first plane and a second plane, and possessing at least one coupling zone in which at least a portion of a first guide is close to a portion of a second guide.

More particularly, the invention concerns a guiding structure comprising:
- a first buffer layer with a first index;
- a first strip with a second index, higher than the first index, located on the first layer;
- a guiding layer with a third index, lower than the second index, covering the first strip and the first buffer layer;
- a second buffer layer with a fourth index covering the guiding layer;
- a second strip with a fifth index, higher than the fourth index, located on the second buffer layer;
- a third buffer layer with a sixth index, lower than the fifth index, covering the second strip and the second buffer layer.

Furthermore, the invention concerns a method for the making of a guiding structure, comprising the following steps:
- a first step for the making, on a substrate, of the first buffer layer;
- a second step for the making of a layer of a material with an index higher than that of the first buffer layer followed by an etching of the first strip;
- a third step for the making, on the first strip and on the first buffer layer, of the guiding layer;
- a fourth step for the making, on the guiding layer, of a second buffer layer;
- a fifth step for the making of a layer of a material with an index higher than that of the second buffer layer followed by an etching of the second strip;
- a sixth step for the making of a third buffer layer on the second strip and the second buffer layer.

BRIEF DESCRIPTION OF THE DRAWINGS

The different objects and features of the invention will appear more clearly from the following description and from the appended drawings, of which.

DETAILED DESCRIPTION OF THE INVENTION

Figure 1:
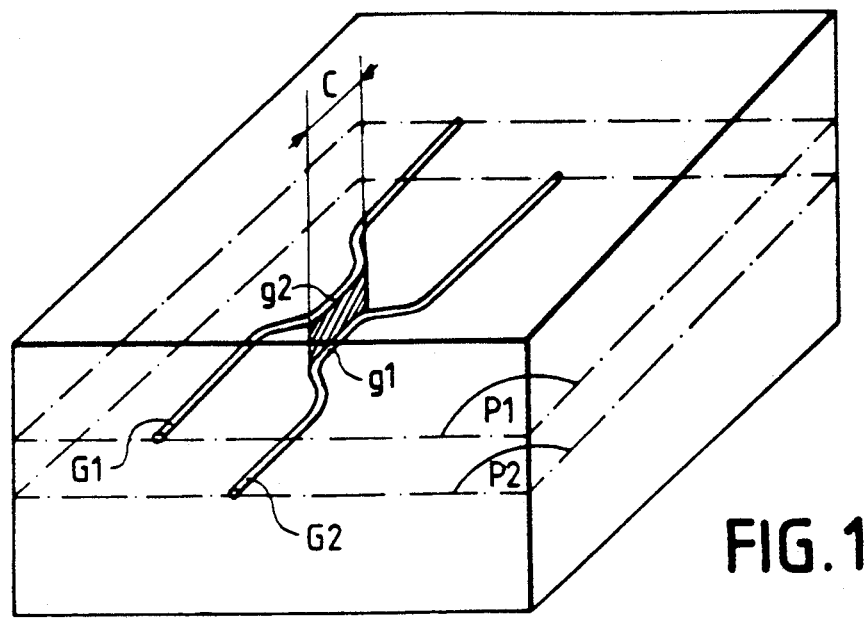
FIG. 1 shows a general embodiment of the device of the invention.

Referring to FIG. 1, we shall firstly describe a general embodiment of the structure of the invention. This structure has a first guide G1 located in a plane P1 of a substrate. A second guide G2 is located in a plane P2 parallel to the plane P1 The two guides include portions g1 and g2 which are close to each other and constitute a coupling zone C. Preferably, these portions g1 and g2 are located in a plane perpendicular to the planes P1 and P2. Under these conditions, the portions g1 and g2 are separated by the distance between the planes P1 and P2. The distance between the planes P1 and P2, which can be easily determined with precision, characterizes the coupling between the portions g1 and g2 of the guides G1 and G2.

Figure 2:
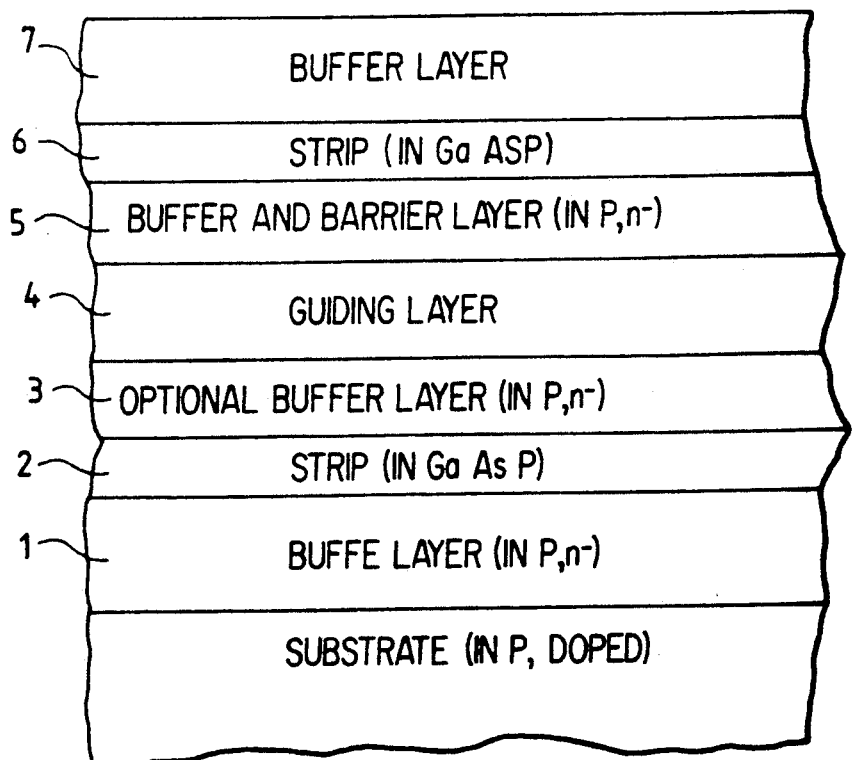
FIG. 2 shows a detailed view of an embodiment, made by means of semiconductor materials, of the device of the invention.

Referring to FIG. 2, we shall now describe a device according to the invention, made of semiconductor material. The semiconductor material will be based on indium and phosphorus, for example.

The device has a buffer layer 1, made of n−doped InP, on a substrate made of doped InP.

Figure 3:
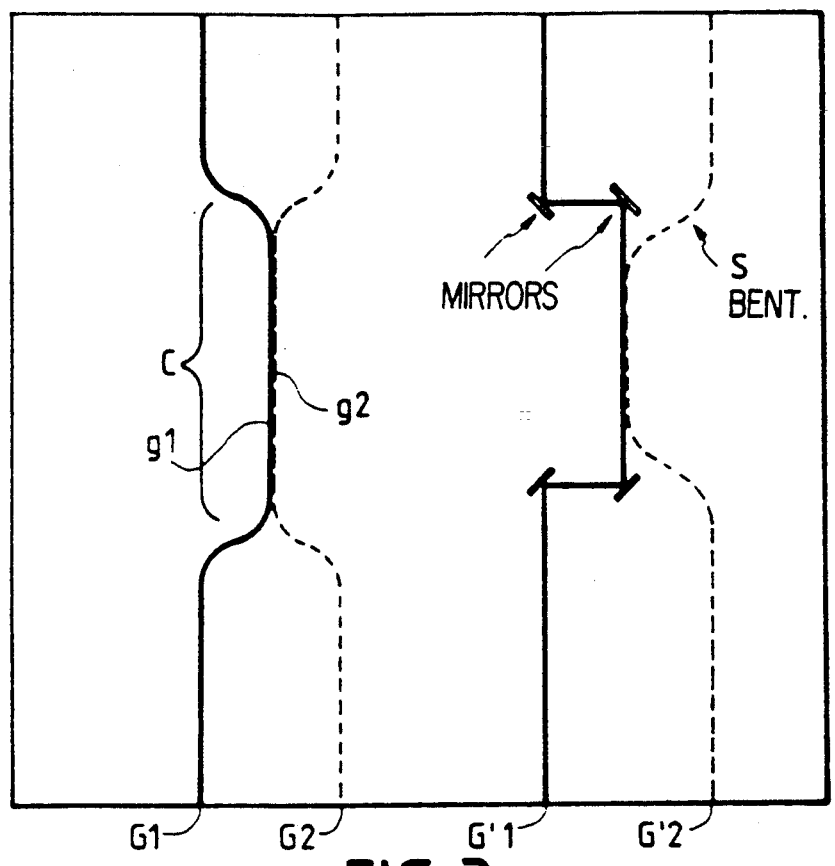
FIGS. 3 to 5 show detailed views of the device of FIG. 2.

A strip 2 is made on this buffer layer 1. This strip 2 is made of InGaAsP, for example, and has a higher refractive index than the material of the buffer layer 1. This strip 2 has a shape such as the one shown in FIG. 3, showing a top view of the device.

The unit formed by the buffer layer 1 and the strip 2 is covered with a buffer layer (3) made of n−doped InP. However, this buffer layer is not necessary in every case.

A guiding layer 4, made of InGaAsP covers the buffer layer (3).

A buffer layer 5, made of n−doped InP covers the guiding layer 4.

A second strip 6, made of InP, with an index higher than that of the material of the layer 5, is made in this buffer layer 5.

The shape of the strip 6 is that shown in FIG. 3.

Finally, the buffer layer 5 and the strip 6 are covered with a buffer layer 7 made of InP.

Each guide has a buried structure, such as the one described in the French patent application No. 86 04523. The two guides are therefore buried at different levels, and are located in different planes of the structure.

The materials used for the different buffer layers will preferably be identical. Similarly, the two strips will be identical in nature.

The non-linear shapes of the strips shown in FIG. 3 enable the making of the couplings between the guides as in the coupling zone C.

Figure 4:
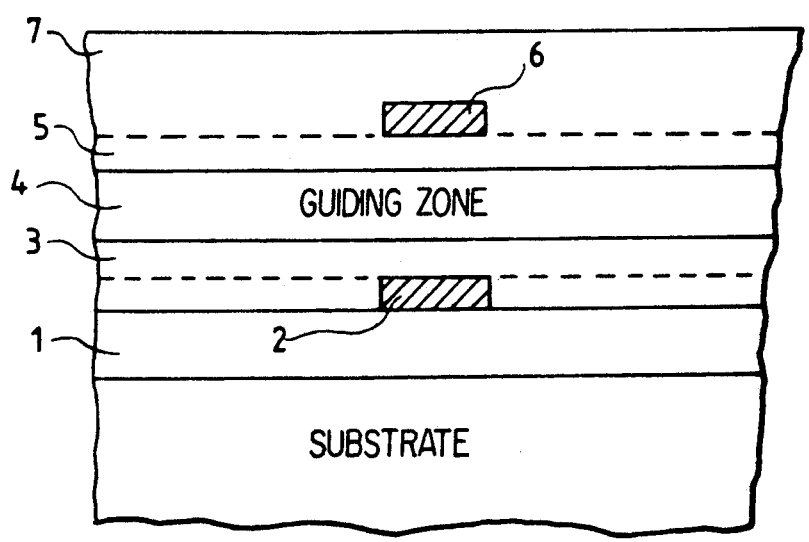
Figure 5:
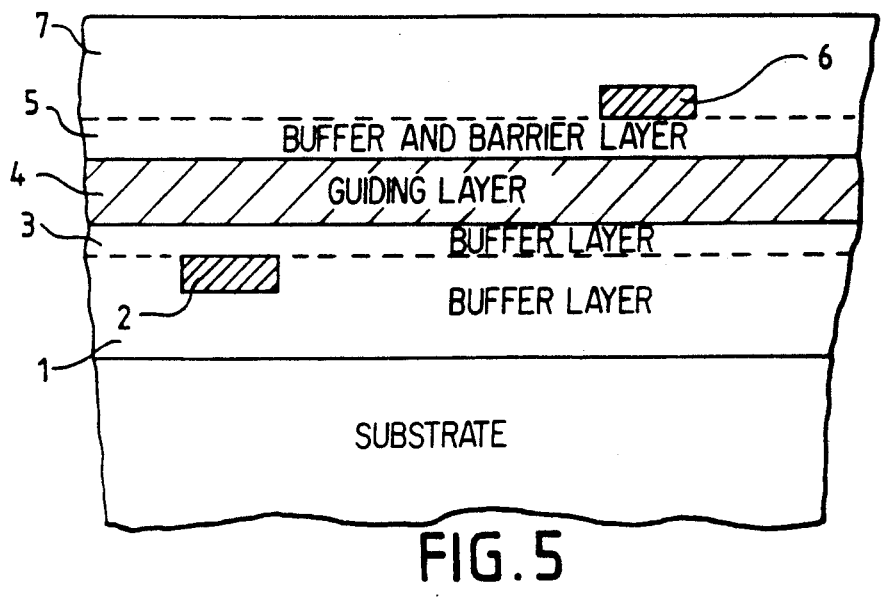

A coupler such as this enables an easy connection of the inputs/outputs of the guides. Indeed in FIG. 4, which shows a section perpendicular to the guides, the points of access to the guides are completely distinct. By contrast, FIG. 5 shows a perpendicular section in the coupling zone C.

The above-described structure may work in two modes, namely an active mode or a passive mode, i.e. with the possibility of applying an electrical field or injecting a current.

As a passive component, this structure enables the separation of the wavelength with very high separating capacity through its very short coupling length which is of the order of several tens of micrometers. Reciprocally, through the access guides, this structure enables the multiplexing of the wavelengths. Thus, the structure enables two points of a volume to be connected. Indeed, the three directions of deflection of the light beam are made possible, firstly, by lithography for the two horizontal directions and, secondly, vertically, by the exchange of energy between the two superimposed guides.

This component may be subjected to an electrical field, by providing for electrodes (not shown) above the guides, and may thus have an operation that depends on the applied field.

The component can be used as a light switch. For this purpose, the electrical field will disturb the exchange of energy and, hence, the coupling length between the two guides. Following the application of an electrical field, the light energy will get switched over from one output guide to the other one. The indices of the layers can be modified by application of an electric field or by injection of charges.

The electric field also enables the adjusting of operation of the structure, as a multiplexer or demultiplexer, to the operating wavelength.

To increase the electric field effects on the structure, the main guiding layer (4) may be a multiple quantum well (MQW) structure. This MQW structure gives additional liberty to the choice of the optic index and gives different, important physical effects in active mode.

In the structure, a non-uniform zone, depopulated of free carriers is created beneath the electric field. The effects of this zone are very great and may be used for the working of the component.

Figure 6:
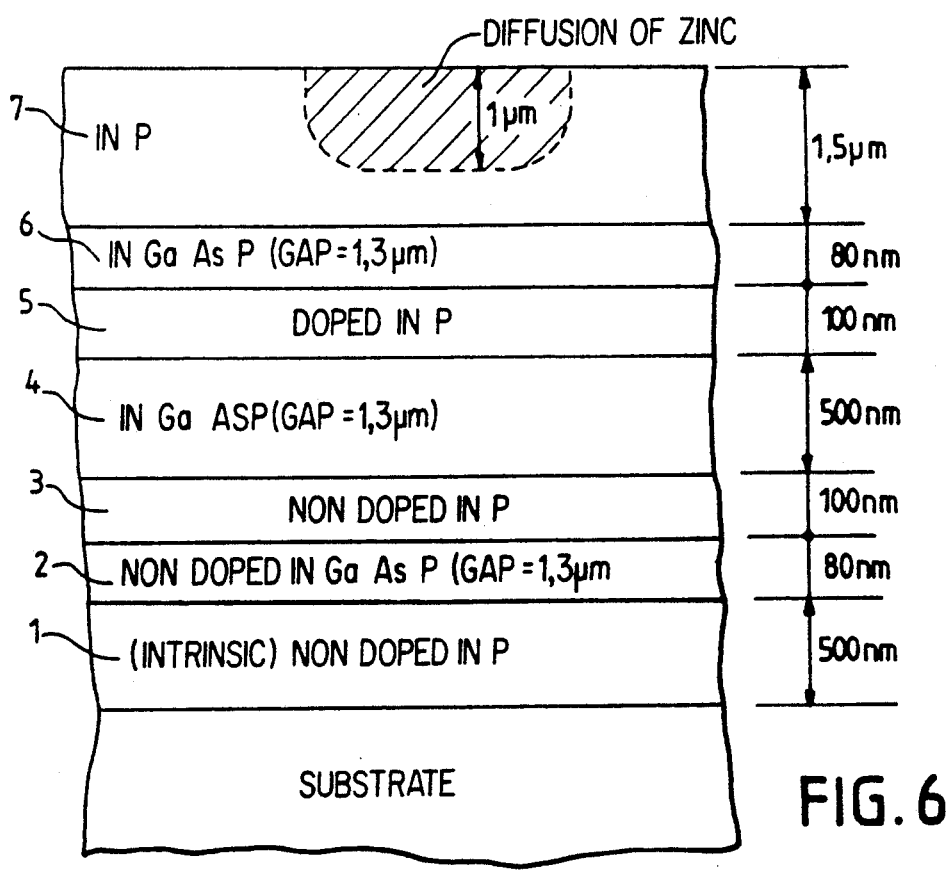
FIGS. 6 and show 7 examples of the structures of the different layers according to the invention.

FIG. 6 gives a detailed view of an exemplary embodiment of the device according to the invention.

The different elements mentioned here above have the following characteristics (in terms of materials and thicknesses):
  substrate: n+doped InP;
  buffer layer 1: (intrinsic) non-doped InP; thickness 500 nm;
  strip 2: non-doped InGaAsP having an energy bandwidth of 953 meV; thickness 80 nm;
  buffer layer 3: non-doped InP; thickness 100 nm;
  main guiding layer 4: non-doped InGaAsP having an energy bandwidth of 953 meV; thickness 500 nm;
  buffer layer 5: non-doped InP, thickness 100 nm;
  strip 6: InGaAsP with an energy bandwidth of 953 meV; thickness 80 nm;
  buffer layer 7: p doped InP; thickness 1500 nm.

The buffer layer 7 has p type doping, by zinc diffusion for example, on a depth of about 1000 nm, to enable a p contact to be set up.

A structure such as this has layers 3 and 5 that are almost identical to each other and strips 2 and 6 that are almost identical to each other. This structure is therefore symmetrical with the main guiding layer 4.

The following is an example of the composition of the strips 2 and 6:

$$*In_{0.72}Ga_{0.28}As_{0.6}P_{0.4}$$

According to one embodiment of the invention, the main guiding layer 4 may constitute a multiple quantum well. For example, this multiple quantum well may be an alternation of InGaAsP and InP layers.

More precisely, it may be formed by:
  30 layers of InGaAsP with an energy bandwidth of 1.55 μm, having the formula:

$$*In_{0.58}Ga_{0.42}As_{0.9}P_{0.1},$$

with a thickness of 8 nm each.
  30 layers of InP with a thickness of 10 nm.

A guiding layer such as this therefore has a thickness of 540 nm.

Figure 7:
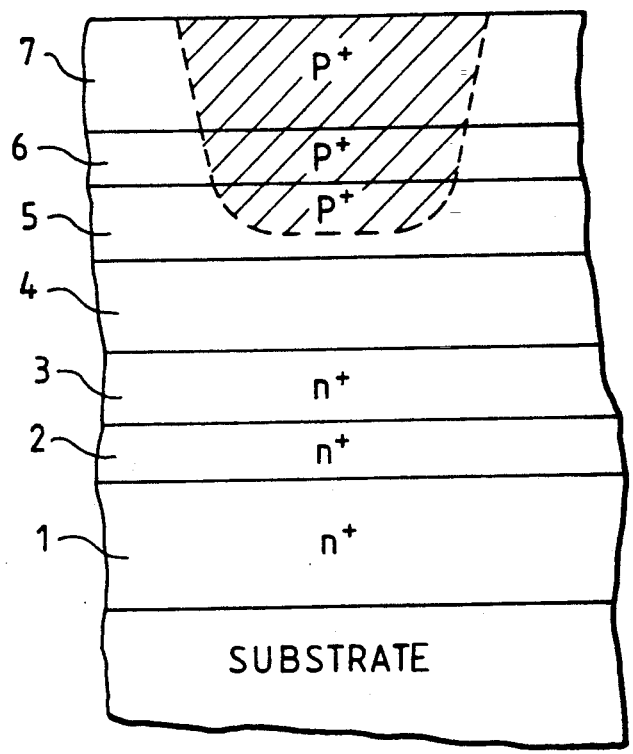

To increase the electric field in the main guiding layer, it is possible to provide the layers 1, 2 and 3 with n+type doping and make a deeper p+type diffusion through the layers 7, 6 and 5 as shown in FIG. 7.

The intrinsic zone 4 and the layers 3 and 5 will get depopulated under a reverse voltage and create index variations.

Figure 8:
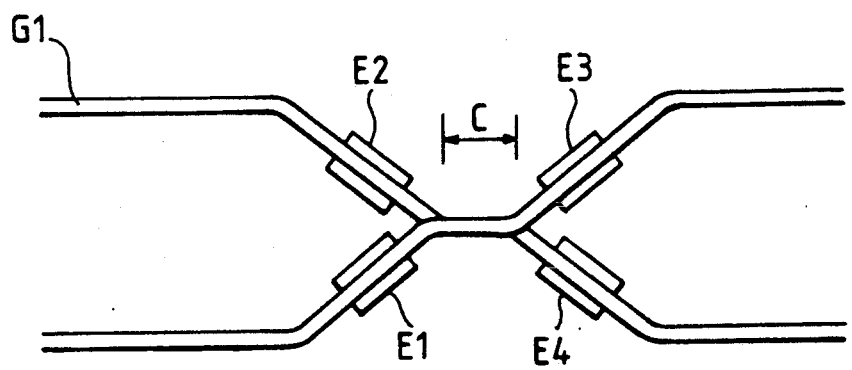
FIG. 8 shows a top view of an alternative embodiment of the device of the invention.

According to the exemplary embodiment of FIG. 8, the two guides G1 and G2 may be made so as to cross each other. Again, the electric field application electrodes (E1, E2, E3, E4) may be located on the guides, on either side of the crossing in the vicinity of the crossing.

We shall now describe a method for the making of the device of the invention.

Starting with a semiconductor substrate (InP for example), MOCVD or MBE deposition techniques are used to deposit a buffer layer 1 and then a second layer made of a different material with an index higher than that of the layer 1. This material can thus be subjected to attack by a chemical solution and will be the strip 2 providing lateral confinement. This strip will have the shape given to it by the mask with an interaction zone and an S-shaped part or it will be provided with mirrors to enable the input or the output of the signal.

After this step, the sample is again placed in a growth unit for renewal of epitaxy. This unit may be different from the first unit used. Then, it is the layer 3 that is deposited as a buffer layer. This layer is not indispensable, but enables the structure to be made symmetrical should this be desired. Then the guiding layer 4, with an optical index higher than that of the buffer layer, is deposited. This layer may be made of the same material as the layer 2 or it may be made of another type of semiconductor material, or else it may be formed by a stack of layers of two types of semiconductor, thus forming a multiple quantum well structure. Then a layer 5, which is a buffer and barrier layer, is deposited and, finally, another layer 6 with a higher index than that of the buffer layers is deposited. This layer may be made of a material different from that of the layer 2, depending on whether a symmetrical structure is desired or not.

The next step is that of a selective chemical attack of the localized layer 6 defining a strip with the planar shape described by the mask. The processing of this layer 6 is similar to that of the layer 2.

The sample is again placed in a growth unit for a deposition of a buffer layer in order to bury the structure to reduces propagation losses and facilitate the technological steps that will be needed for the electrical contacts.

What is claimed is:

1. A 3D integrated guiding structure comprising:
   at least two waveguides nonoverlappingly positioned respectively in a first plane and a second plane, said first and second planes being parallel to one another; and possessing at least one coupling zone in which at least a portion of a first guide is positioned above a portion of a second guide.

2. A guiding structure according to claim 1, wherein the portions of the first and second guides are located in a third plane perpendicular to the first and second planes.

3. A guiding structure wherein, outside the portions of the coupling zone, the guides are contained in two planes substantially equidistant to the third plane and perpendicular to the first and second planes.

4. A guiding structure according to claim 1 comprising:
   a first buffer layer with a first index;
   a first strip with a second index, higher than the first index, located on the first layer;
   a guiding layer with a third index, lower than the second index, covering the first strip and the first buffer layer;
   a second buffer layer with a fourth index covering the guiding layer;
   a second strip with a fifth index, higher than the fourth index, located on the second buffer layer;
   a third buffer layer with a sixth index, lower than the fifth index, covering the second strip and the second buffer layer.

5. A guiding structure according to claim 4, comprising a fourth buffer layer located between the first strip and the guiding layer.

6. A guiding structure according to claim 4, wherein the first, second, third and fourth buffer layers are made of similar materials.

7. A guiding structure according to claim 6, wherein the strips are made of similar materials with indices higher than those of the materials of the buffer layers.

8. A guiding structure according to claim 5, wherein the second and fourth buffer layers have the same composition, doping and thicknesses and wherein the first and second strips have the same composition, doping and dimensions so that the structure has a symmetry with respect to the guiding layer.

9. A guiding structure according to claim 4, wherein the guiding layer is made in the form of an alternation of layers constituting a multiple quantum well.

10. A guiding structure according to claim 4, wherein the first and second strips form a coupling zone in which the strips have portions located in a plane perpendicular to the planes of the layers.

11. A guiding structure according to claim 4, comprising:
    said first strip being located in a first plane;
    said second strip being located in a second plane parallel to said first plane; and
    a coupling zone of said first strip and said second strip in which a portion of said first strip is disposed over a portion of said second strip.

12. A guiding structure according to claim 4, comprising:
    said first and second portions being located in a third plane arranged perpendicular to said first and second planes; and
    second portions of said first and second strips, other than said portions of said first and second strips, being located in fourth and fifth planes each being perpendicular to said first and second planes and positioned on either side of and equidistant to said third plane.

* * * * *